United States Patent
Doubler et al.

(10) Patent No.: US 6,692,530 B2
(45) Date of Patent: Feb. 17, 2004

(54) SPLIT SLEEVE MODULAR JOINT

(75) Inventors: Robert L. Doubler, Ida, MI (US); John E. Hammill, Sr., Rossford, OH (US)

(73) Assignee: Hammill Manufacturing Co., Toledo, OH (US)

( * ) Notice: Subject to any disclaimer, the term of this patent is extended or adjusted under 35 U.S.C. 154(b) by 0 days.

(21) Appl. No.: 09/982,448

(22) Filed: Oct. 17, 2001

(65) Prior Publication Data

US 2003/0074078 A1 Apr. 17, 2003

(51) Int. Cl.[7] ............................ A61F 2/32; A61F 2/36
(52) U.S. Cl. ................................ 623/22.42; 606/62
(58) Field of Search .................. 623/20.15, 20.25, 623/22.11, 22.42, 22.45, 22.46, 23.15, 23.18, 23.21, 23.22, 23.23, 23.25, 23.26, 23.27, 23.29, 23.31, 23.45, 23.46, 23.47; 606/62, 63, 64; A61F 2/28, 2/30, 2/32, 2/36

(56) References Cited

U.S. PATENT DOCUMENTS

| 4,419,026 A | | 12/1983 | Leto | |
|---|---|---|---|---|
| 4,706,367 A | * | 11/1987 | Garringer | ..................... 29/526 |
| 5,516,335 A | * | 5/1996 | Kummer et al. | ............... 606/63 |
| 5,653,765 A | | 8/1997 | McTighe et al. | |
| 5,876,459 A | | 3/1999 | Powell | |
| 6,193,725 B1 | * | 2/2001 | Macey | ......................... 606/104 |
| 6,193,759 B1 | * | 2/2001 | Ro et al. | .................. 623/23.28 |
| 6,355,069 B1 | * | 3/2002 | DeCarlo, Jr. et al. | ..... 623/23.26 |
| 6,428,578 B2 | * | 8/2002 | White | ...................... 623/23.22 |

FOREIGN PATENT DOCUMENTS

| DE | 3609120 A1 | * | 9/1987 | ............ A61F/2/28 |
|---|---|---|---|---|
| DE | 0 290 735 A1 | * | 11/1988 | ............ A61F/2/36 |
| DE | 40 31 520 A1 | * | 4/1992 | ............ A61F/2/30 |
| FR | 2 772 595 A1 | * | 6/1999 | ............ A61F/2/46 |
| GB | 2 347 353 A | * | 6/2000 | ............ A61F/2/36 |
| WO | WO 98/55051 A1 | * | 12/1998 | ............ A61F/2/36 |
| WO | WO 00/30569 A1 | * | 6/2000 | ............ A61F/2/36 |
| WO | WO 02/05732 A1 | * | 1/2002 | ............ A61F/2/30 |

* cited by examiner

*Primary Examiner*—David H. Willse
*Assistant Examiner*—Javier G. Blanco
(74) *Attorney, Agent, or Firm*—McHale & Slavin, P.A.

(57) ABSTRACT

A modular prosthesis has an intramedullary rod element which is to be inserted in a bone, an artificial trochanter and a neck for carrying the ball. The intramedullary rod has a proximal end and a distal end telescoped together allowing free relative rotation of the ends. A split sleeve is fitted between the telescoped portions of the rod to form a rigid connection when the ends are separated longitudinally. A jack screw within the intramedullary rod separates the proximal end from the distal end.

14 Claims, 5 Drawing Sheets

SPLIT SLEEVE MODULAR JOINT

This application is related to an application entitled, Split Ring Bone Screw for a Spinal Fixation System, Ser. No. 09/981,961, by the same inventors, filed on even date herewith.

FIELD OF THE INVENTION

This invention relates to the medical field of orthopaedics and joint replacement, in particular. Modular artificial joints have several components that must be assembled and placed in the patient to reconstruct a joint. While modular joints provide the ability to custom fit an artificial joint to a patient's anatomy, the connection between the components must be without relative movement after implantation. This invention is directed to a modular artificial joint construction which provides a locking mechanism to secure the components immovably together.

BACKGROUND OF THE INVENTION

Artificial joints or prosthesis have now been constructed for almost every natural joint in the living body. As the medical field gains more understanding of the problems involved in mating inanimate constructions with animate tissue and designing mechanical devices that can duplicate natural movement, the number of implantations will continue to increase. In addition to the major joints, such as the hip, knee, shoulder, elbow, wrist and ankle, better engineering of the prosthesis, accompanied with miniaturization, will permit smaller and smaller natural joints, e.g. vertebrae, phalanges and tarsals, to be reconstructed. Until now, the larger joints have received the most attention mainly because of the larger size of the bones. The prosthesis of this invention may be utilized in all joints.

In replacing a hip joint, the head of the femur is removed along with the ball. The trochanter portion of the femur is shaped and prepared for receiving the prosthesis so that the artificial joint will closely approximate the natural hip.

Earlier artificial hip joints were made of one-piece construction requiring a large inventory of prosthesis to accommodate the various sized patients. The modular artificial joint has two or three or more elements which replace the natural hip. By manufacturing these components with interchangeable connections but different external sizes, inventories may be smaller because of the ability to mix and match components. Also, the modular prosthesis provides more flexibility in customizing the various components of a joint to the various parts of a patient's natural joint.

In a three piece artificial hip joint, the various sized components of the joint that may be selected are the intramedullary rod, the trochanter and the neck. The intramedullary rod is inserted into the end of the femur. The rod acts as a stabilizer in maintaining the artificial joint in the axis of the femur. The upper portion of the rod which extends out of the femur is fitted into a trochanter element which is shaped like the removed broad head of the femur which it replaces. This element, along with the rod, is used to adjust the length of the prosthesis to approximate the natural length of the femur.

The natural trochanter is the broadened area offset from the end of the femur. The natural trochanter may be at any radial angle about the axis of the femur. This natural angular relationship must be reproduced by the intramedullary rod and the artificial trochanter. The artificial trochanter is seated on the end of the patient's femur and is the main load bearing element of the prosthesis. It is important that this load, which is mostly compression, is transmitted along the axis of the femur.

A neck element is inserted into the trochanter element and carries an extension onto which the ball joint will be fixed. The horizontal angle between the trochanter and the neck extension is variable to reproduce the anteversion angle of the patient's natural joint. The neck carries cantilevered forces in torque and compression between the acetabulum and the trochanter. It is also important that these forces do not result in relative movement between the trochanter and the neck.

All these elements have a central bore and are permanently secured together by a bolt which is inserted into the neck element, extends through the trochanter element, and is threaded into the upper end of the rod. In some cases, the intramedullary rod may be attached to the bone with bone cement while, in other cases the cement is omitted.

When the cement is omitted, the placement and fixation of the intramedullary rod becomes more critical to pain free usage of the prosthesis. Further, it is most important that the intramedullary rod not be disturbed after insertion since this would corrupt the union between the rod and the interior of the femur.

In order to maintain the original union between the femur and the intramedullary rod, modular prosthesis have been developed to allow rotational adjustment of the several parts or elements about the emplaced rod during the placement of the prosthesis to more closely reproduce the natural structure of the hip. It has been found that, in some cases, as the intramedullary rod has been inserted into the bone canal, there is rotational movement of the rod. In order to preserve the union between the rod and the bone, there must be a mechanism to accommodate the changed angular orientation of the proximal end of the intramedullary rod so that the prosthesis closely approximates the natural trochanter and ball.

While the above description refers to a modular hip prosthesis, substantially the same considerations must be given to other modular prosthesis, such as a knee prosthesis in which an intramedullary rod is placed in the lower end of the femur and in the upper end of the tibia or the elbow in which an intramedullary rod is placed in the lower end of the humerus and the upper end of the radius or ulna. Because of individual physical anomalies, the functional prosthesis must be capable of angular adjustment to conform to the natural physique.

With the advantage of flexibility gained by modular prosthesis, there comes the requirement that there be no movement between the several parts or elements after implantation. These movements may cause misalignment of the joint resulting in increased pain, trauma to the joint and, even, dislocation of the joint.

DESCRIPTION OF THE PRIOR ART

The prior art is replete with artificial prosthesis and hip joints, in particular.

Illustrative of the state of the art is U.S. Pat. No. 5,876,459 to Powell which discloses a modular hip joint having a stem, one end of which is inserted in the intramedullary canal. The other end of the stem is tapered to fit within a second, neck, element. The neck ultimately supports the ball joint. A sleeve element is placed over the junction of the first two elements. All three elements are rotationally movable relative to each other. A bolt is driven through the bore of the neck and stem deforming a portion of the interconnected elements for a friction fit between the neck and the stem. These prior art patents disclose that the sleeve may have a polygonal shaped bore with the articulating elements having corresponding shaped portions. The interconnected elements of these hip joints do not form a static lock between each other but require a deformation of one or more elements before a friction fit is established. The deformation and friction fit is between the stem and the neck rather than the sleeve and the stem.

U.S. Pat. No. 5,653,765, to McTighe et al discloses a modular hip joint with a stem, an intermediate shoulder portion, and a proximal shoulder piece which attaches to the ball. The stem and the intermediate shoulder portion have interengaging teeth on the corresponding ends of each by which they are connected. This end-to-end connection allows for rotational movement of the elements relative to each other. The proximal shoulder piece and the intermediate shoulder piece also have an end-to-end toothed connection for rotational adjustment. This construction has two movable end-to-end connections which provide good flexibility for rotation of the elements but have small surface areas of fixation to each other limited to the surfaces of the interengaged teeth.

The Leto patent, U.S. Pat. No. 4,419,026 issued Dec. 6, 1983, discloses a resilient split sleeve camming lock for use with telescoping tubular elements. The system relies on the resilience of the split ring and does not require a permanent deformation of the split sleeve by longitudinal displacement.

SUMMARY OF THE INVENTION

In the instant invention a modular prosthesis is taught which has an intramedullary rod element which is to be inserted in a bone. The rod has a shaped proximal portion which is telescoped into one end of a bore in the weight-bearing element which is the artificial trochanter in the hip prosthesis. The mating surfaces of the shaped rod and the weight-bearing element bore are shaped to permit 360° rotation of the rod within the bore. The wall shapes of the proximal portion of the rod and the bore are complimentary but of different sizes to accommodate a split sleeve disposed between the rod and the bore. This mechanism allows the trochanter to be rotated on the distal end of the intramedullary rod without disturbing the placement of the rod in the intramedullary canal.

Upon relative longitudinal movement between the bore and the rod a rotationally immovable connection is formed between the intramedullary rod and the weight-bearing element or trochanter. The artificial ball element is telescoped into the other end of the trochanter bore permitting additional rotational adjustment. All the elements are locked together by a bolt through the neck and rod.

In a particularly preferred embodiment of the instant invention a modular prosthesis is described for use as a joint prosthesis having an intramedullary rod, a weight-bearing component and a artificial ball. The intramedullary rod has a distal end adapted for insertion into the intramedullary canal of the femur and a proximal end. The proximal end includes a screw threaded throughbore along the longitudinal axis of the intramedullary rod.

The weight-bearing component has a narrow distal end and a larger proximal end forming an external shape approximating the natural bone. The weight-bearing component has a through bore from the distal end to the proximal end, with the proximal end of the through bore having a smooth circumference. The distal end of the through bore has a circumference with opposite planar sides joined by curved surfaces. The circumference of the trochanter bore and the circumference of the proximal end of the intramedullary rod telescope together with the opposite planar surfaces in intimate contact with each other forming a rotationally secure connection with the artificial trochanter approximating the position of the natural trochanter.

The ball element has a planar distal end with a through bore. There is a cylindrical extension about the through bore adapted to be inserted into the proximal end of the through bore of the artificial trochanter. The extension and the wall of the trochanter bore may have complimentary shapes to interlock without rotational movement. Alternatively, there may be a key lock formed as a pin fitting into an aperture on the opposing contacting surfaces of the ball element and the trochanter. The proximal end of the through bore in the neck has an enlarged countersunk bore and the distal end of the through bore telescopes over the proximal end of the intramedullary rod. A screw threaded bolt is disposed in the countersunk bore and threadably engaged with the screw threads in said proximal end of said intramedullary rod forming a locked integral prosthesis.

Accordingly, it is an objective of the instant invention to provide a joint with an intramedullary rod element which is connected with the weight-bearing element in such a manner as to provide infinite rotational adjustment therebetween. Rotational movement, in this context, refers to the turning of either element in a plane normal to the common longitudinal axis of the elements.

It is another objective of the instant invention to provide a locking mechanism between the intramedullary rod and the weight-bearing element to permanently fix the components together after rotational adjustment.

It is a further objective of the instant invention to provide a connection between the trochanter element and the intramedullary rod in such a manner as to limit the combined length of the elements.

It is a further objective of the instant invention to provide the trochanter and the neck with a locking mechanism to rigidly secure the components together to prevent relative rotation.

It is a still further objective of the invention provide a locking mechanism between the neck element and the trochanter element that permits rotational adjustment of the anteversion angle.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Figure 1A:
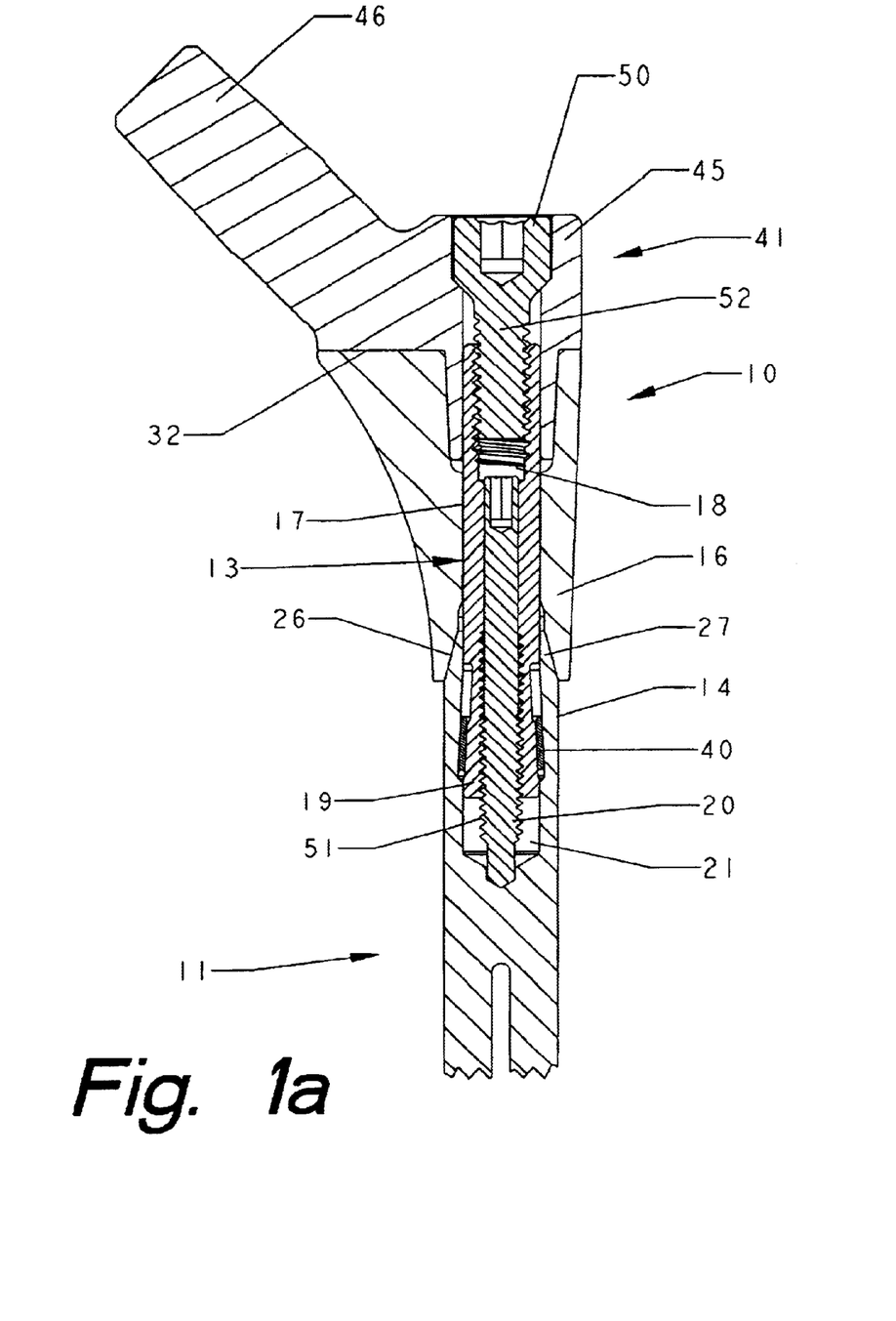
FIGS. 1a, 1b, and 1c are views of the prosthesis of this invention partly in section.
Figure 1B:
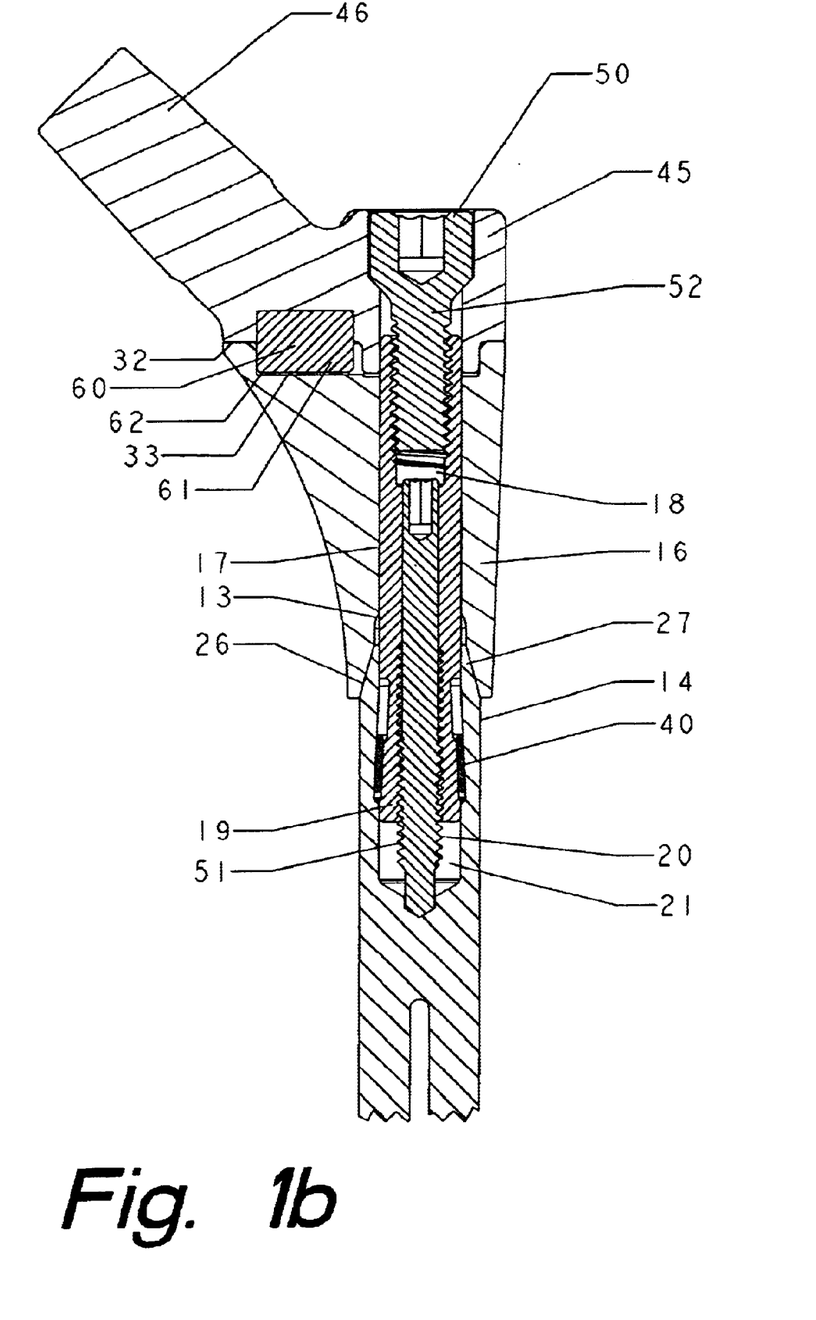
Figure 1C:
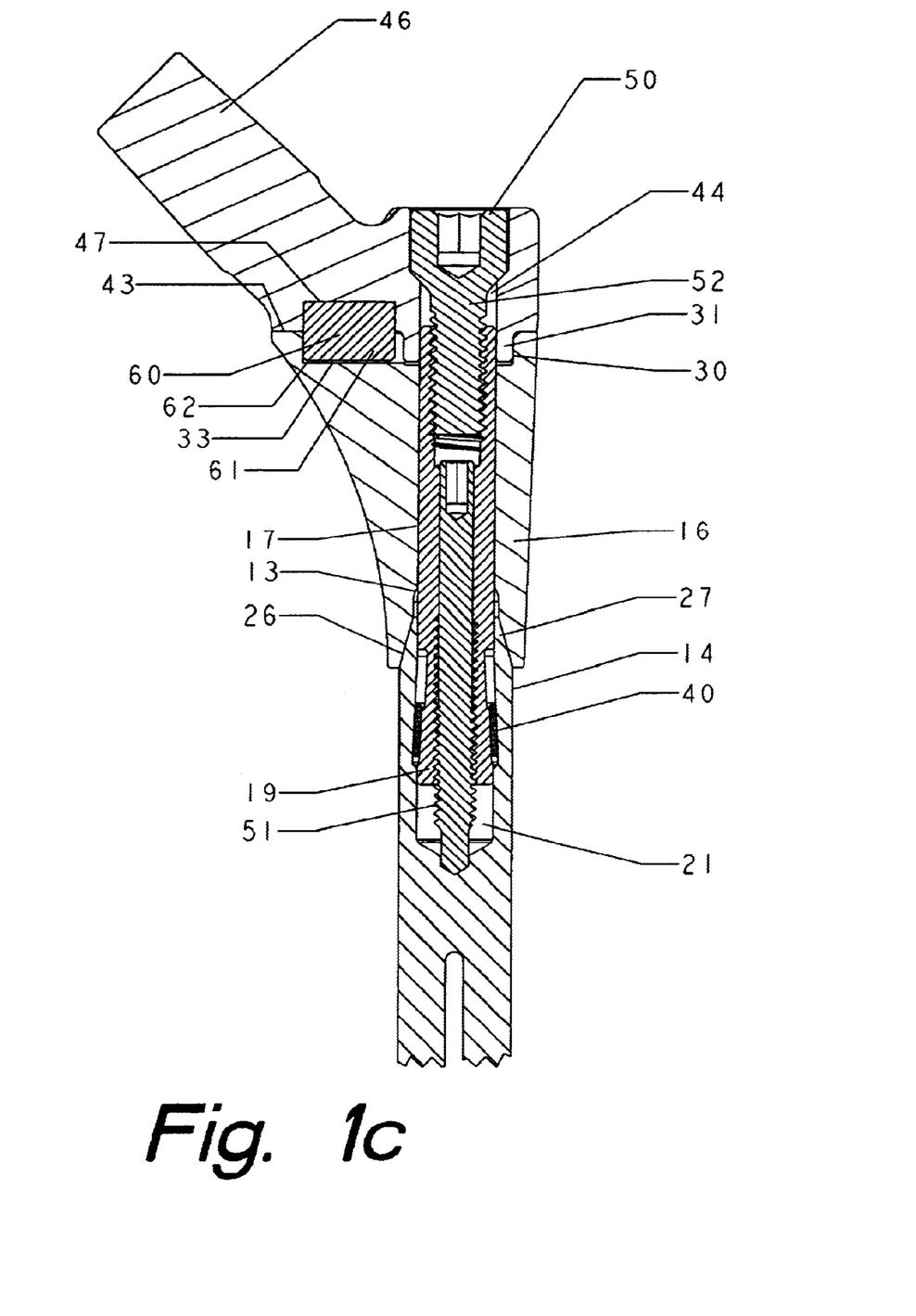

The prosthesis 10, shown in FIG. 1, has an intramedullary rod 11 which provides stability. The rod has a distal end 12 and a proximal end 13. The proximal end of the rod is smaller in diameter than the distal end. The distal end 12 is inserted into the patient's femur and forms the stabilizing connection for maintaining the prosthesis in alignment with the axis of the femur. The distal end of the rod may have flutes 15 to increase the surface area of the junction between the rod and the intramedullary canal of the femur. The distal end of the rod may also have a slot(s) 14 along the longitudinal axis of the rod to better accommodate the internal anomalies occurring in the interior of the intramedullary canal. This structure allows the distal end of the rod to compress to a smaller diameter to more easily reach the desired depth of insertion. Further, to accommodate the anatomy, the intramedullary rod may have an arcuate shape, shown in FIG. 3.

Figures 2, 3:
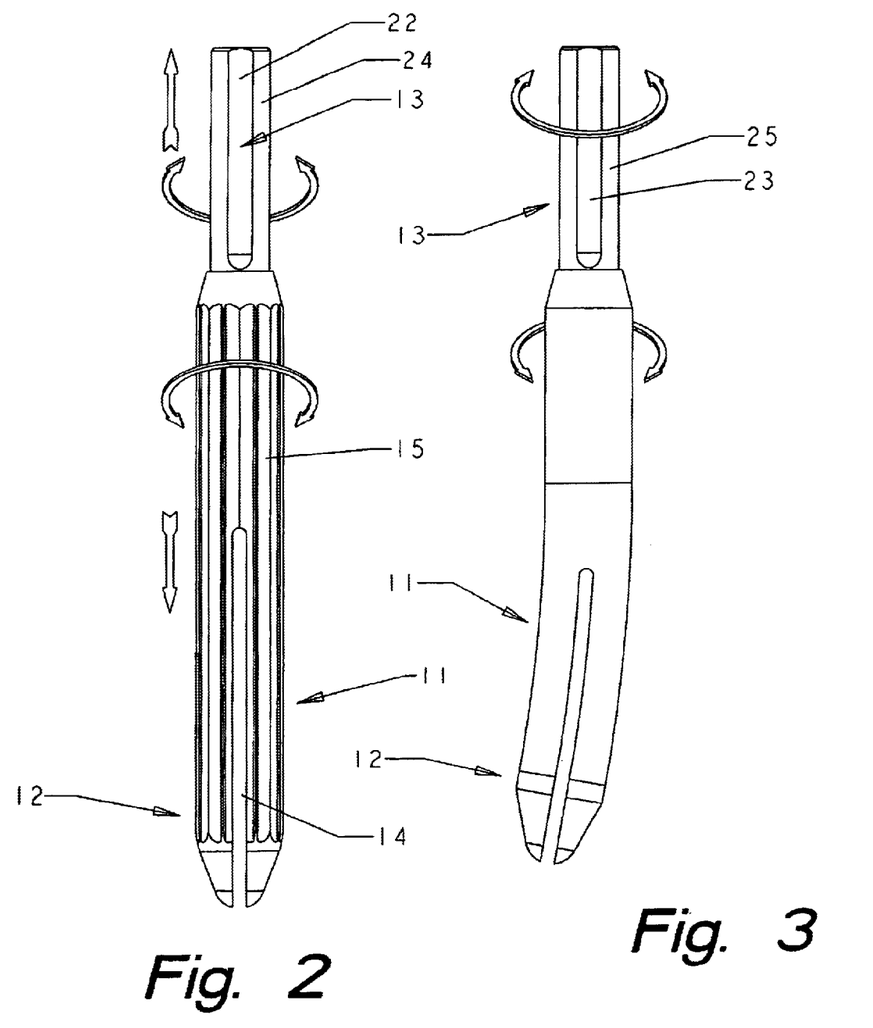
FIG. 2 shows a prospective view of one embodiment of the intramedullary rod.
FIG. 3 is a perspective view of another embodiment of the intramedullary rod of this invention.
Figure 4:
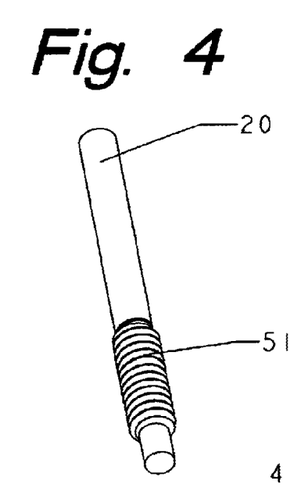
FIG. 4 shows a perspective of the jack screw used in this invention.

The trochanter element 16 is mounted on the proximal end of the intramedullary rod. The trochanter has a through bore portion 17 in the distal end thereof through which the proximal end 13 of the intramedullary rod is inserted. As shown in FIG. 2, the proximal end 13 of the intramedullary rod has corresponding mating surfaces which lock the elements together preventing any rotational movement. The bore portion 17 has planar opposite sides and curved surfaces joining the ends of the planar sides. The proximal end of the intramedullary rod is sized to closely fit within the bore portion 17. The proximal end of the intramedullary rod also has opposite planar sides 22 and 23 joined by curved surfaces 24 and 25.

Because the intramedullary rod 11 and trochanter 16 do not move rotationally, it is very important that the angular orientation of the trochanter be established during insertion of the rod into the femur. In FIG. 1, the proximal end 13 of the intramedullary rod is shown fixed in the distal end 12 by a split sleeve connector 40. The split sleeve 40, shown in FIG. 5, has an inner wall 41 and an outer wall 42 and a gap 43. The sleeve is resilient and may be made from the same biocompatible materials as the remainder of the prosthesis. The sleeve may be cylindrical or conical. Before the split sleeve 40 is fixed in position, the proximal and distal ends of the intramedullary rod may, each, be rotated freely about their longitudinal axis. This allows infinite angular adjustment of the proximal end of the intramedullary rod which, in turn, orients the angle of the trochanter without stress on the connection between the distal end of the rod and the intramedullary canal. Then the inner wall 41 of the sleeve is pressed onto the outer surface of the lower portion of proximal end 13. The outer wall 42 is pressed against the inner surface of a blind bore 21.

As mentioned earlier, these components may be provided in different lengths and diameters. The proper insertion of the rod allows the immovable connection of the trochanter to the intramedullary rod in the approximate original position of the excised head of the femur.

In addition to or in place of the complementary surfaces in bore 17 and the proximal end 13 of the intramedullary rod, the bore portion 17 may be formed with a taper 26 which is smaller toward the proximal end of the trochanter and larger at the distal end. The proximal end of the intramedullary rod may be formed with a slightly larger diameter taper 27 having a smaller end toward the proximal end. As the two elements are telescoped together, the tapered walls engage each other further strengthening the connection between the elements. This additional support is desired when the trochanter 16 is formed of an interconnecting cellular structure to promote bone ingrowth.

The cooperating tapers 26 and 27 establish a precise limit to the distance the trochanter may be telescoped over the intramedullary rod. This limit, in turn, establishes the overall length of the two elements. Alternatively or in addition, the proximal end of the intramedullary rod may have and external shoulder (not shown) of greater diameter which may seat against the distal end of the trochanter to establish overall length and additional support.

The proximate end 13 of the intramedullary rod has a through bore 18 with internal threads 52 in the upper portion for receiving the threaded end of bolt 50 securing the neck 46 to the trochanter 16 and internal threads 19, in the lower portion, cooperating with a threaded jack screw 20.

Figures 5, 6:
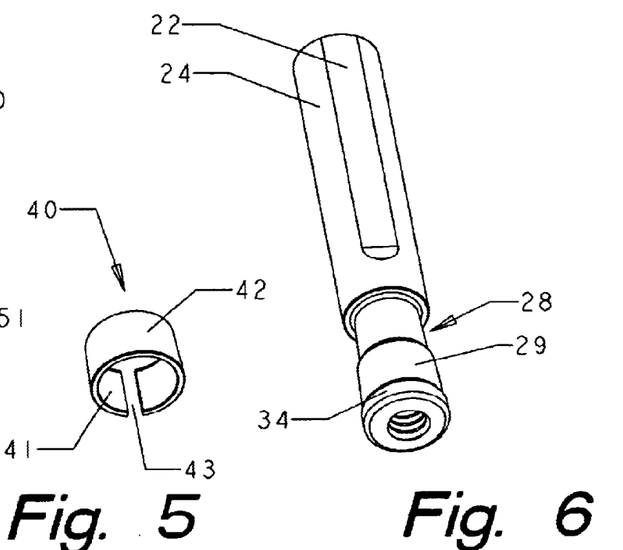
FIG. 5 shows a prospective of the split sleeve of this invention.
FIG. 6 shows a perspective of the proximal end of the intramedullary rod of this invention.

The external wall of the lower portion of the proximal end 13 has a smaller diameter area 28, shown in FIG. 6, allowing installation of the split sleeve 40 about the circumference of the lower portion of proximate end 13. The lower portion has a larger diameter portion 29 which engages the split sleeve 40 during longitudinal translation. The lower portion terminates in an enlarged shoulder 34 that forms a seating surface for the sleeve. The jack screw 20 cooperates with blind bore 21 in the distal end of the intramedullary rod to longitudinally translate the proximal end 13 as the threads 51 of the jack screw are rotated within threads 19. As the jack screw is rotated by an implement (not shown) inserted in the through bore 18, split sleeve 40 is press fit between the external wall of the proximal end 13 and the internal wall of the distal end 12 of the intramedullary rod. The jack screw can be removed or it may remain in the prosthesis. While a jack screw is shown and described, other mechanical devices may be used to pull or push the proximal end and the distal end into a press fit with the split sleeve.

The internal wall of the distal end is conical, with the smaller diameter toward the mouth of the blind bore 21. Therefore, the more the jack screw is tightened, the more compression is applied to the press fit between the proximal end and the distal end of the intramedullary rod. Ultimately, the proximal and distal ends of the intramedullary rod are rigidly connected to each other. As shown and described, the proximal end of the intramedullary rod is telescoped into the distal end of the intramedullary rod, obviously the telescoped components could be reversed.

The proximal end of trochanter 16 has a counter bore portion 30 which has a greater diameter than the diameter of the through bore portion 17 in the distal end. Counter bore portion 30 receives the distal end 31 of the neck element 46. This counter bore portion 30 may be cylindrical or conical. If conical, the walls of the counter bore portion 30 taper from a large diameter proximal end toward the distal end.

The counter bore portion 30 establishes a rotationally adjustable connection with the neck 46. This telescoped connection permits the prosthesis to be adjusted, after the intramedullary rod has been inserted into the femur, to approximate the natural location of the original ball.

The trochanter 16 is shaped like the natural femur head and has an outer diameter that is larger than the intramedullary rod at the distal end. The distal end of the trochanter is inserted into the intramedullary canal. This junction of the trochanter and the shaft of the femur is the primary load carrying connection between the prosthesis and the patient's body. The trochanter flares to a larger diameter proximal end which has a planar surface 32 containing the counter bore portion 30. The bore 30 includes a linear portion forming a recess or diametrical extension 33. The recess or bore extension 33 receives the tang 61 of the key lock 60 to establish the anteversion angle between the trochanter and the neck. The bore extension 33 is formed as an extension of the counter bore 30, however the recess 33 may be separated from the bore.

The neck 46 has a partially cylindrical body 41 with a laterally extending arm extending from the proximal surface of the body 41. This arm carries the ball joint (not shown) for an artificial hip and can be specifically set at different anteversion angles to the trochanter and thus the axis of the femur with the key lock 60.

The distal surface of the neck is formed as a flat surface 43 with a depending smaller diameter distal end 31. The flat surface 43 is in intimate contact with the surface 32 of the trochanter, as shown in FIG. 1. A recess or blind bore 47 is formed in the surface 43. The recess has a geometrical shape which prevents movement of an inserted key. In FIGS. 1 and 3 the geometrical shape is illustrated as triangular but other shapes are possible.

A key lock 60 having the same peripheral configuration as the recess is placed in the recess 47. The key lock 60 has a base 61 with a thickness equivalent to or less than the depth of the recess 47. A tang 62 is formed on the base 61. The tang 62 is shaped to closely fit into the linear extension 33 in the trochanter 16. The tang has a height approximately the same as the depth of the extension 33.

The drawings illustrate one embodiment of the invention in which the base of the key lock cooperates with the blind bore in the neck and the tang cooperates with the recess in the trochanter to stop rotation. However, this organization can be reversed with the base of the key lock cooperating with the trochanter and the tang with the neck.

The tangs may be located on the base at different angular orientations, such as, a neutral orientation of the tang. The tang may be disposed at approximately +12 degrees rotation (right) from neutral. To provide a suitable anteversion angle range of key locks, a preferred set of key locks has each tang set at one degree (1) increments, both + (right) and − (left) from neutral, resulting in a complete set of twenty five (25) key locks.

The distal end 31 is telescoped into the counter bore portion 30 of the trochanter. The outer surface of the distal end may be cylindrical or conical. The conical surface of the distal end 31 tapers from a smaller distal end toward the surface 43. The base of the conical pin is slightly larger than the through bore portion 30 so that a friction fit is established when the elements are telescoped together. This maintains the rotational axis relationship between the elements.

The neck has a bore 44 extending from the proximal end through the distal end 31. The proximal end 45 of the bore 44 is countersunk to receive the head of the bolt 50. The distal end of bore 44 receives the proximal end 13 of the intramedullary rod 11.

The prosthesis may be assembled without compromising the union between the intramedullary canal and the intramedullary rod. After the distal end of the rod is seated in the canal, the proximal end of the rod is placed in the blind bore of the distal end.

Prior to the joining of the proximal end and the distal end or the rod, the proximal end has the split sleeve resiliently encircling the lower portion of the proximal end and the jack screw threaded in place in the through bore of the proximal end. The proximal end of the rod can then be freely rotated to orient the shaped surfaces of the proximal end resulting in angular fixation of the position of the artificial trochanter upon telescoping onto the proximal end. Optionally, the artificial trochanter may be already placed on the shaped upper portion of the proximal end and both the trochanter and the proximal end are freely rotated to the desired orientation.

The jack screw can then be inserted into the assembled components and, if turned in place, is turned to engage the end of the blind bore in the distal end or the rod. Upon continued turning the proximal end of the rod is longitudinally translated in relation to the distal end. The causes the split sleeve to engage both the proximal end and the distal end in ever increasing pressure. Upon insuring that the press fit is secure, the intramedullary rod with the properly oriented trochanter are ready for assembly with the neck component.

The upper surface of the trochanter and the lower surface of the neck may be planar providing universal rotation between the components. As shown and described, the upper surface of the trochanter and the lower surface of the neck have counter bores to accept a key lock to further insure non-rotation between the components. In either case, once the anteversion angle of the neck is set, a bolt is inserted into the through bore of the neck. By turning the threads of the bolt 50 into the threads 52 of the intramedullary rod these cooperating screw threads tighten and the elements of the prosthesis are drawn together forcing the tapered distal end of the neck into a friction fit with the tapered bore of the trochanter and the trochanter to a stop limit with the intramedullary rod. In the final disposition, the trochanter and the intramedullary rod a locked together over a major part of the length of each. And the neck is locked to the rotationally immovable trochanter at a specific anteversion angle.

The various elements or components of the prosthesis may be made in different external sizes so that a range of elements is available to meet the size needs of various patients. However, the interconnecting portions of the different sized components are of the same size or, at least, made in a range of sizes so that the different external sized elements may be securely connected as described above.

We claim:

1. In a modular hip prosthesis kit including a plurality of different sized intramedullary rods, trochanters, and necks, said plurality of intramedullary rods, trochanters, and necks being adapted for interchangeable assembly to form a particular hip prosthesis with specific characteristics, said specific characteristics including a longitudinal axis and an anteversion angle, said angle fixed by rotational adjustment of said intramedullary rods, trochanters and necks about the longitudinal axis, the improvement comprising said intramedullary rods each having a proximal end and a distal end, each of said proximal ends and said distal ends adapted to be telescoped together for rotational movement, each of said proximal ends having a bore with internal threads, each of said distal ends having a blind bore, a plurality of split sleeves each adapted to be disposed between a telescoped proximal end and distal end, each of said split sleeves adapted to rigidly fix said proximal end and said distal end upon longitudinal translation of said proximal end and said distal end, a plurality of bolts and a plurality of jack screws, each of said jack screws adapted to be threaded in said threaded bore of each of said proximal end and contacting said blind bore of each of said distal ends whereby turning of said jack screw compresses said slit sleeve, and each of said bolts adapted to be threaded in said threaded bore of each of said proximal end and adapted to engage each of said necks whereby turning of said bolts rigidly joins each of said trochanters and each of said distal ends.

2. A modular hip prosthesis kit of claim 1 wherein each of said proximal ends has an upper end and a lower end and a bore therethrough, said lower end having a reduced diameter portion, said split sleeve carried by said reduced diameter portion, each of said distal ends having a blind bore, said blind bore having a conical wall, whereby longitudinal translation of each of said proximal end and each of said distal end compresses said split sleeve between said lower end and said conical wall.

3. A modular hip prosthesis kit of claim 1 wherein each of said distal ends is adapted for insertion in the femur and each of said proximal ends has a reduced diameter with a screw threaded bore, each of said trochanters have an enlarged proximal end and a smaller distal end with a through bore, said through bore adapted for telescoping connection with said proximal end of any one of said intramedullary rods, each of said necks having a proximal end carrying an arm and a distal end with an extension, each of said necks having a through bore, one end of said through bore housed in said extension, said extension adapted to telescope into said through bore at said proximal end of any of said trochanters, and each bolt is adapted to be placed in the through bore of said neck, and extend through the through bore of said trochanter and be threaded into the threaded bore of said intramedullary rod to form a specific prosthesis.

4. A method of assembly of a hip prosthesis to closely approximate a natural hip, said prosthesis having an intramedullary rod with a proximal end and a distal end, a trochanter with a throughbore rotationally fixed on said proximal end of said intramedullary rod, and a neck with a throughbore rotationally fixed on said trochanter opposite said intramedullary rod comprising the steps of a) establishing a fixed position of the distal end of said intramedullary rod;

b) providing said throughbore of said trochanter and said proximal end of said intramedullary rod with complementary shaped surfaces;

c) mounting said trochanter on said proximal end of said intramedullary rod in a fixed rotational relationship;

d) telescoping said proximal end of said intramedullary rod into said distal end of said intramedullary rod;

e) freely rotating said telescoped portion of said proximal end of said intramedullary rod in said distal end of said intramedullary rod to obtain the desired radial orientation of said trochanter;

f) providing said telescoped portion of said proximal end of said intramedullary rod with a reduced diameter portion and mounting a split sleeve on said reduced diameter portion;

g) providing said telescoped portion of said distal end of said intramedullary rod with a conical blind bore; and h) separating said telescoped portion of said proximal end and said distal end of said intramedullary rod longitudinally to press fit said split sleeve between said proximal end and said distal end of said intramedullary rod resulting in a rigid connection.

5. A method of assembly of a hip prosthesis as claimed in claim 4 further comprising the steps of i) providing said proximal end of said intramedullary rod with internal screw threads to accept a bolt;

j) placing said neck on said trochanter opposite said intramedullary rod with said throughbore about said proximal end of said intramedullary rod;

k) rotationally adjusting said neck to approximate the desired anteversion angle; and l) tightening a bolt in said internal screw threads of said proximal end of said intramedullary rod to rotationally fix said neck to said trochanter.

6. A modular prosthesis to be used in bone joint replacement having a neck, a weight bearing component with a through bore, and an intramedullary rod for securing said weight bearing component to the bone, said intramedullary rod having a proximal end adapted to rotationally fit within said through bore, said proximal end having an upper portion and a lower portion, a bore through said upper portion and said lower portion, said bore having internal threads, said intramedullary rod having a distal end adapted for insertion in a bone canal, said distal end adapted to telescope into said through bore of said weight bearing component, a blind bore in said distal end, said lower portion of said proximal end disposed in said blind bore, and a split ring in said blind bore encircling said lower portion of said proximal end, a jack screw in said threaded bore of said proximal end, said jack screw contacting said blind bore, whereby turning said jack screw translates said proximal end relative to said distal end compressing said split ring between said proximal end and said distal end of said intramedullary rod.

7. A modular prosthesis of claim 6 wherein a bolt is adapted to be threaded in said upper portion of said proximal end of said intramedullary rod, said bolt engaging said weight bearing component whereby turning said bolt translates said weight bearing component and said distal end of said intramedullary rod relative to each other forming a friction fit between said weight bearing component and said distal end of said intramedullary rod.

8. A modular prosthesis of claim 6 wherein the walls of said blind bore are tapered whereby turning of said jack screw increases compression.

9. A modular prosthesis of claim 6 wherein said lower portion of said proximal end is tapered whereby turning of said jack screw increases compression.

10. A modular prosthesis of claim 6 wherein said weight bearing component and said distal end of said intramedullary rod have complementary telescoped surfaces, said surfaces limiting said telescoping movement.

11. A modular prosthesis of claim 6 wherein said weight bearing component and said distal end of said intramedullary rod have complementary telescoped surfaces, said surfaces preventing relative rotational movement.

12. A modular hip prosthesis comprising a neck for attaching an artificial ball, an artificial trochanter and an intramedullary rod, said neck having a bore, said artificial trochanter having a bore, said intramedullary rod having a proximal end and a distal end, said proximal end having a through bore, said through bore having internal threads, said distal end having a blind bore, said distal end of said intramedullary rod adapted to be inserted into the shaft of the femur, said artificial trochanter telescoped onto said distal end of said intramedullary rod and adapted to contact said femur, said proximal end of said intramedullary rod rotationally disposed in said bore of said artificial trochanter, said proximal end of said intramedullary rod having an upper portion and a lower portion, a split ring disposed about said lower portion, said lower portion disposed in said blind bore of said distal end of said intramedullary rod, a jack screw threaded in said through bore and in contact with said blind bore, whereby turning said jack screw translates said proximal end relative to said distal end and compresses said split ring to form a friction fit, said neck connected to said artificial trochanter by said bolt, said bolt threaded in said through bore whereby turning said bolt translates said neck and said distal end of said intramedullary rod relative to one another to lock said prosthesis in place.

13. A modular hip prosthesis of claim 12 wherein said blind bore is tapered.

14. A modular hip prosthesis of claim 12 wherein said bore of said artificial trochanter and said distal end of said intramedullary rod have complementary surfaces preventing rotational movement and determining translation distance.

* * * * *